(12) United States Patent
Carlsson

(10) Patent No.: US 11,045,635 B2
(45) Date of Patent: Jun. 29, 2021

(54) MALE FLUID CONNECTOR, A FEMALE FLUID CONNECTOR AND A FLUID CONNECTION SYSTEM COMPRISING THE SAME

(71) Applicant: GAMBRO LUNDIA AB, Lund (SE)

(72) Inventor: Ola Carlsson, Lund (SE)

(73) Assignee: Gambro Lundia AB, Lund (SE)

( * ) Notice: Subject to any disclaimer, the term of this patent is extended or adjusted under 35 U.S.C. 154(b) by 758 days.

(21) Appl. No.: 15/571,375

(22) PCT Filed: Apr. 26, 2016

(86) PCT No.: PCT/EP2016/059281
§ 371 (c)(1),
(2) Date: Nov. 2, 2017

(87) PCT Pub. No.: WO2016/174032
PCT Pub. Date: Nov. 3, 2016

(65) Prior Publication Data
US 2019/0117950 A1    Apr. 25, 2019

(30) Foreign Application Priority Data

Apr. 30, 2015 (SE) .................................... 1550543-1

(51) Int. Cl.
*A61M 39/10* (2006.01)
*A61M 1/14* (2006.01)
*A61M 1/36* (2006.01)

(52) U.S. Cl.
CPC .............. *A61M 39/10* (2013.01); *A61M 1/14* (2013.01); *A61M 1/367* (2013.01);
(Continued)

(58) Field of Classification Search
CPC .... A61M 39/10; A61M 39/1011; A61M 1/14; A61M 1/3661; A61M 1/367;
(Continued)

(56) References Cited

U.S. PATENT DOCUMENTS

| 5,947,937 A | 9/1999 | Urrutia et al. |
| 2008/0287919 A1 | 11/2008 | Kimball |

(Continued)

FOREIGN PATENT DOCUMENTS

| WO | 2008/009946 | 1/2008 |
| WO | 2012024370 | 2/2012 |

(Continued)

OTHER PUBLICATIONS

ISO 594-1:1986 "Conical fittings with a 6% (Luer) taper for syringes, needles and certain other medical equipment Part 1: General requirements," dated Jun. 15, 1986.

(Continued)

*Primary Examiner* — Philip R Wiest
(74) *Attorney, Agent, or Firm* — K&L Gates LLP

(57) ABSTRACT

A male fluid connector, a female fluid connector, and a connection system comprising the connectors. The connection system comprises a male connector and a female connector that both are modified such that they cannot be engaged. The connection system removes the risk of unintentional connection of the two modified connectors not intended to be connected but still allows connection of the two modified connectors to other non-modified connectors.

17 Claims, 7 Drawing Sheets

(52) U.S. Cl.
CPC ... *A61M 1/3661* (2014.02); *A61M 2039/1094* (2013.01); *A61M 2205/6009* (2013.01)

(58) Field of Classification Search
CPC .. A61M 2039/1016; A61M 2039/1077; A61M 2039/1083; A61M 2039/1088; A61M 2039/1094; A61M 2205/6009
See application file for complete search history.

(56) References Cited

U.S. PATENT DOCUMENTS

| | | |
|---|---|---|
| 2009/0099552 A1 | 4/2009 | Levy et al. |
| 2009/0299339 A1* | 12/2009 | Young .................. A61M 39/10 604/535 |
| 2010/0283238 A1 | 11/2010 | Deighan et al. |
| 2011/0306940 A1 | 12/2011 | Miyasaka |
| 2013/0245611 A1 | 9/2013 | Bonnet et al. |

FOREIGN PATENT DOCUMENTS

| | | |
|---|---|---|
| WO | 2012134513 | 10/2012 |
| WO | 2012170961 | 12/2012 |
| WO | 2013173157 | 11/2013 |
| WO | 2014177630 | 11/2014 |

OTHER PUBLICATIONS

ISO 594-2:1998 "Conical fittings with 6% (Luer) taper for syringes, needles and certain other medical equipment-Part 2: Lock fittings," dated Sep. 1, 1998.

ISO 8637:2014, British Standards Publication, "Cardiovascular implants and extracorporeal systems—Haemodialysers, haemodiafilters, haemofilters and haemoconcentrators (ISO 8637:2010, including Amendment 1 Apr. 1, 2013)," Jan. 2014.

ISO 8638:2014, British Standards Publication, "Cardiovascular implants and extracorporeal systems—Extracorporeal blood circuit for haemodialysers, haemodiafilters and haemofilters," Mar. 31, 2014.

ISO 80369-1:2010, "Small-bore connectors for liquids and gases in healthcare applications—Part 1: General requirements," Dec. 15, 2010.

ISO/DIS 80369-7:2013, "Small-bore connectors for liquids and gases in healthcare applications Part 7: Connectors with 6% (Luer) taper for intravascular or hypodermic applications," Jul. 2013.

International Search Report issued in International Patent Application No. PCT/EP2016/059281 dated Sep. 20, 2016.

Written Opinion issued in International Patent Application No. PCT/EP2016/059281 dated Sep. 20, 2016.

International Standard ISO 594/1, "Conical fittings with a 6 % (Luer) taper for syringes, needles and certain other medical equipment Part 1: General requirements," First Edition Jun. 15, 1986, 10 pages.

International Standard ISO 594/2, "Conical fittings with a 6 % (Luer) taper for syringes, needles and certain other medical equipment Part 2: Lock fittings," Second edition Sep. 1, 1989, 16 pages.

BSI Standards Publication ISO 8637:2010, including Amendment 1, "Cardiovascular implants and extracorporeal systems—Haemodialysers, haemodialters, haemofilters and haemoconcentrators," Apr. 1, 2013, 34 pages.

BSI Standards Publication Iso 8638:2014, "Cardiovascular implants and extracorporeal systems—Extracorporeal blood circuit for haemodialysers, haemodialters and haemofilters," Jan. 2014, 26 pages.

International Standard ISO 80369-1, "Small-bore connectors for liquids and gases in healthcare applications—Part 1: General requirements," First Edition, Dec. 15, 2010, 24 pages.

Draft International Standard ISA/DIS 80369-7, "Small-bore connectors for liquids and gases in healthcare applications Part 7: Connectors with 6% (Luer) taper for intravascular or hypodermic applications," downloaded Apr. 27, 2015, 50 pages.

* cited by examiner

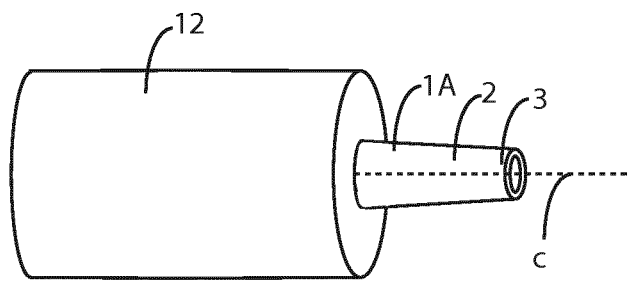
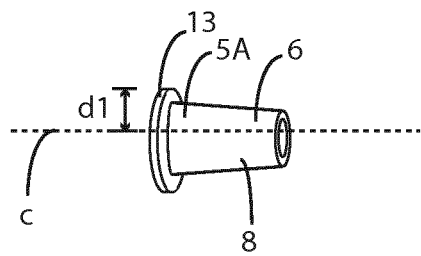
FIG. 1A  FIG. 1B
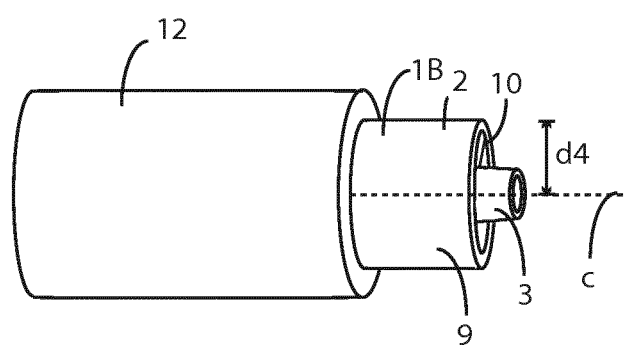
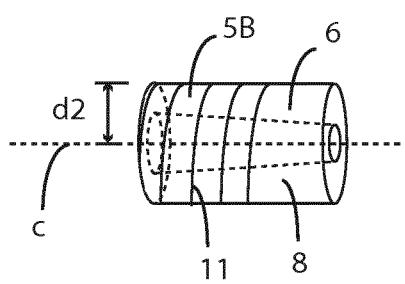
FIG. 1C  FIG. 1D

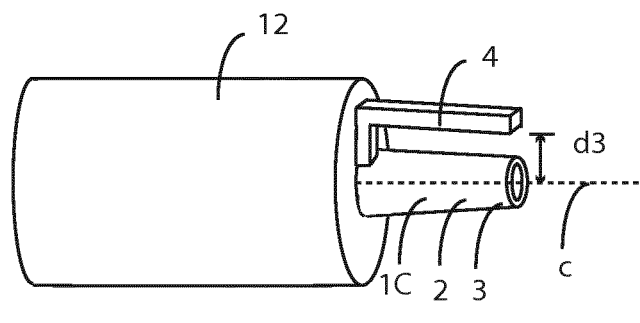
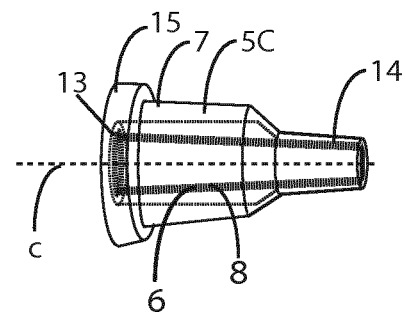
FIG. 2A
FIG. 2C
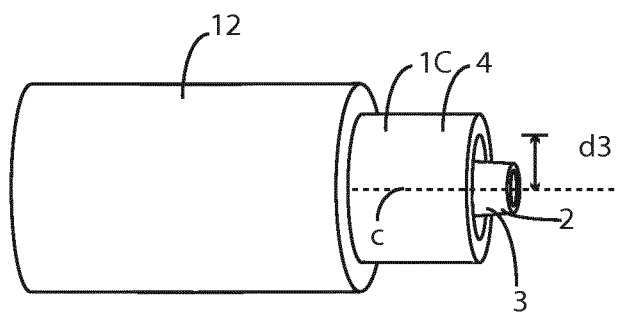
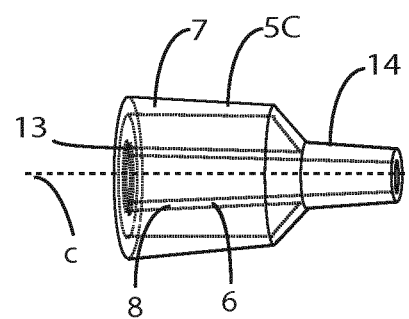
FIG. 2B
FIG. 2D
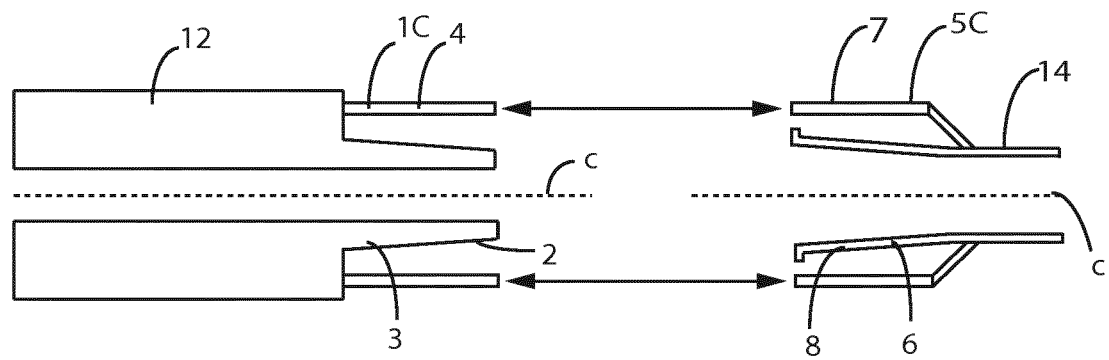
FIG. 2E
FIG. 2F

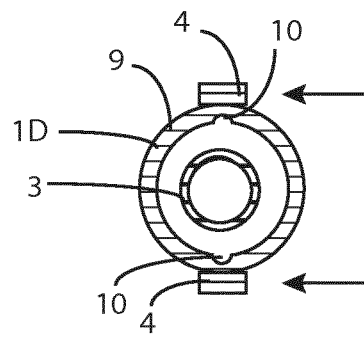
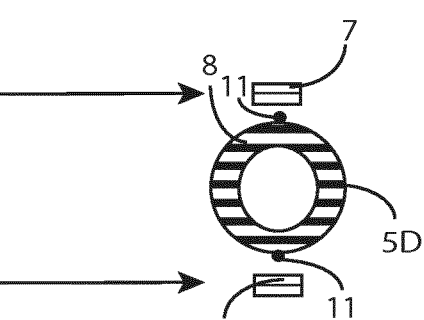
FIG. 4A                FIG. 4B
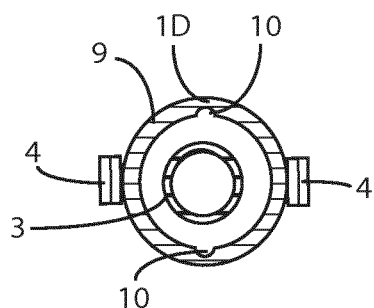
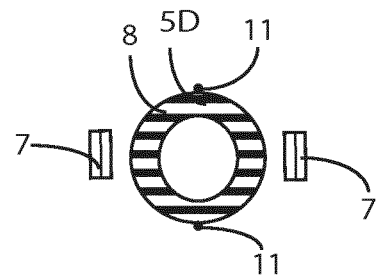
FIG. 4C                FIG. 4D
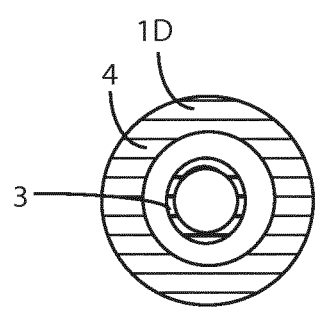
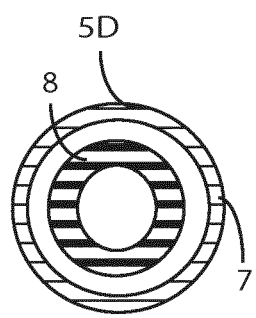
FIG. 4E                FIG. 4F

MALE FLUID CONNECTOR, A FEMALE FLUID CONNECTOR AND A FLUID CONNECTION SYSTEM COMPRISING THE SAME

PRIORITY CLAIM

The present application is a National Phase of International Application No. PCT/EP2016/059281, filed on Apr. 26, 2016, which claims priority to Swedish Patent Application No. 1550543-1, filed on Apr. 30, 2015, the entire contents of each of which are being incorporated herein by reference.

TECHNICAL FIELD

The present invention relates to the field of fluid connectors, and in particular connectors for medical applications such as connection of fluid lines and fluid bags in connection with blood treatment systems and connection of a needle to a syringe.

BACKGROUND

In medical applications it is common to use standardized connectors such as Luer connectors according to ISO 594-1:1986, ISO 594-2:1998, ISO 80369-1:2010 or ISO/DIS 80369-7:2013, or connectors according to ISO 8637:2014 or ISO 8638:2014, where it is desired to connect two entities for transfer of fluid. A Luer connection comprises an interconnecting female part and a male part, the male part being received as a friction fit within the female part, or by a lock fit accomplished by threads. Thanks to the standardized nature of the Luer connector, products with such connectors will still fit together even if they have different manufacturers. However, as the connectors are widely used, they may be erroneously connected to the wrong device such as the wrong fluid bag, fluid line or syringe. A situation with an erroneously connected device may become life threatening, especially when medical care is brought to the patient's own home without continuous supervision from medical expertise. Also in intensive care units the situation with critically ill patients and an overall stressful environment increases the risk of misconnection, for example when using CRRT (Continuous Renal Replacement Therapy).

To avoid making misconnections, it is common to for example colour match the connector of a fluid line to an intended fluid bag with fluid to be delivered via the fluid line, together with careful instructions which fluid bag to be used. This solution has the drawback that it is still possible to make an erroneous connection as there is no structure stopping the engagement of the connectors.

A plurality of solutions to the problem have been disclosed where the connectors have been modified such that a modified female part will only fit with a thereto appropriately modified male part. From U.S. Pat. No. 5,947,937A a method and apparatus is known for preventing mismatching of blood types between a blood bag and a patient. A first and a second connector must have matching configuration coding in order to sealably connect and deliver blood to the patient, thereby preventing mismatch. From US2008/0287919A1 a Luer-like non-standard medical fluid connector is known, that cannot be engaged with a standard Luer fitting. The female and the male connectors are here modified to fit only with each other, the male connector is unable to receive a standard female Luer fitting and the female connector is unable to engage with a standard male Luer fitting.

From WO2012170961A1 a plurality of devices and systems for coupling of fluid lines are known. The devices and systems either have multiple connectors or a single non-round connector. The selectivity of the multiple connectors or single non-round connector requires a certain mutual orientation of the connectors in order to create a complete and non-leaking connection.

The above mentioned solutions delimit the use of such modified connection systems to certain applications.

SUMMARY

It is an objective of the disclosure to alleviate at least some of the drawbacks with the prior art. It is a further objective to provide a connection system that removes the risk of unintentional connection of two connectors not intended to be connected but still allowing connection of the connectors to other connectors. It is a further object to provide a connection system that is easy and cheap to manufacture. It is a still further objective to provide a connection system with as little modification as possible to an existing connection system.

These objectives and others are at least partly achieved by the connectors and connection system according to the independent claims, and by the embodiments according to the dependent claims.

According to a first aspect, the disclosure relates to a male single channel fluid connector for a medical application comprising a male connector body defining a hollow male portion. The male connector body has a first structure exterior of the hollow male portion allowing rotational engagement of the male connector body with a female single channel fluid connector of a first type with a hollow female portion in order to form a fluid tight connection, but preventing any engagement with a female single channel fluid connector of a second type with a hollow female portion having a second structure exterior of the hollow portion. The first structure is designed to match the second structure such that any engagement is prevented.

According to one embodiment, the rotational engagement includes rotating at least one of the hollow male portion and the hollow female portion of the female single channel fluid connector of the first type in relation to each other while inserting the hollow male portion inside the hollow female portion in order to create the fluid tight connection.

According to one embodiment, the first structure has a shape of a layer of a first material.

According to one embodiment, the first structure extends beyond the hollow male portion in a direction of engagement with the female single channel fluid connector.

According to one embodiment, the first structure extends at least partly around the circumference of the hollow male portion.

According to one embodiment, the first structure is divided into at least two first structure parts spaced apart around the circumference of the hollow male portion.

According to one embodiment, the first structure extends around the whole circumference of the hollow male portion.

According to one embodiment, the first structure has a same length along the male connector body as the length of the hollow male portion.

According to one embodiment, the male connector is made in one piece.

According to one embodiment, the hollow male portion is an inner hollow male portion, and the male connector body is further defining an outer collar surrounding the hollow male portion and spaced radially therefrom, the outer collar is internally threaded, wherein the first structure is extending radially from the exterior of the outer collar. According to one embodiment, the hollow male portion has a tapered shape.

According to a second aspect, the disclosure relates to a female single channel fluid connector for a medical application comprising a female connector body defining a female hollow portion. The female connector body has a second structure exterior of the female hollow portion allowing rotational engagement within the female connector body with a male single channel connector of a first type with a hollow male portion in order to form a fluid tight connection, but preventing engagement with a male single channel connector of a second type with a hollow male portion having a first structure exterior of the hollow male portion, wherein the second structure is designed to match the first structure such that any engagement is prevented.

According to one embodiment, the rotational engagement includes rotating at least one of the hollow female portion and the hollow male portion of the male single channel connector of the first type in relation to each other while inserting the hollow male portion inside the hollow female portion in order to create the fluid tight connection.

According to one embodiment, the second structure at least partly extends around the circumference of the female portion.

According to one embodiment, the second structure extends beyond the female hollow portion in a direction of engagement.

According to one embodiment, the second structure is divided into at least two second structure parts spaced apart around the circumference of the female hollow portion.

According to one embodiment, the second structure has a shape of a sleeve.

According to one embodiment, the second structure has a same length along the female connector body as the length of the female hollow portion.

According to one embodiment, the female connector is made in one piece.

According to one embodiment, the female hollow portion has an external thread.

According to one embodiment, the female hollow portion has a tapered shape.

According to a third aspect, the disclosure relates to a fluid connection system for a medical application comprising a male single channel fluid connector of a first type with a male connector body defining a hollow male portion, and a female single channel fluid connector of a first type with a female connector body defining a hollow female portion. The system further includes a male single channel fluid connector is of a second type with a male connector body having a first structure exterior of a hollow male portion allowing rotational engagement of the male connector body with a female single channel fluid connector of the first type with a hollow female portion in order to form a fluid tight connection. The system further includes a female single channel connector of a second type with a female connector body having a second structure exterior of a hollow female portion allowing rotational engagement within the female connector body with the first type of male single channel fluid connector with the hollow male portion in order to form a fluid tight connection, but preventing any engagement with the second type of male single channel fluid connector with the first structure. The first structure of the second type male single channel fluid connector is designed to match the second structure of the second type female single channel fluid connector such that engagement is prevented between the second type male single channel fluid connector and the second type female single channel fluid connector.

According to one embodiment, the hollow male portion of the second type male single channel fluid connector is an inner hollow male portion, and the male connector body is further defining an outer collar surrounding the hollow male portion and spaced radially therefrom, and the outer collar is internally threaded. The first structure is extending radially from the exterior of the outer collar, and the female hollow portion of the second type female single channel fluid connector has an external thread.

According to one embodiment, the first structure and the second structure are designed such that the first structure and the second structure radially and circumferentially at least partly overlap when a center line c of the second type male single channel fluid connector and the second type female single channel fluid connector, respectively, are aligned and a thread opening of the internal thread of the second type male single channel fluid connector is aligned with a thread start of the external thread of the second type female single channel fluid connector.

According to another embodiment, an inner radius of the second structure is greater than an outer radius of the outer collar but smaller than an outer radius of the first structure, and an outer radius of the second structure is greater than the outer radius of the outer collar.

According to a fourth aspect, the disclosure relates to a system including the fluid connection system, and further including an arterial line and a venous line connected to a blood treatment unit, a dialysis fluid line connected to the blood treatment unit for infusion of dialysis fluid from a dialysis fluid bag, an effluent fluid line connected to the blood treatment unit for passing effluent fluid to an effluent fluid bag, an infusion fluid line connected to the arterial line for infusion of fluid from an infusion fluid bag or anticoagulant fluid bag, and a post replacement fluid line connected to the venous line for infusion of replacement fluid from a replacement fluid bag. The dialysis fluid line is arranged with a female single channel fluid connector of the second type, the dialysis fluid bag is arranged with a male single channel fluid connector of the first type, the effluent fluid line is arranged with a female single channel connector of the second type, the effluent fluid bag is arranged with a male single channel fluid connector of the first type, the infusion fluid line is arranged with a female single channel fluid connector of the first type, the infusion fluid bag or anticoagulant bag is arranged with a male single channel fluid connector of the second type, the post replacement fluid line is arranged with a female single channel fluid connector of the second type and the replacement fluid bag is arranged with a male single channel fluid connector of the first type. The system may for example be a line set or a disposable system.

The herein disclosed connectors are single channel fluid connectors meaning that each connector is only arranged with one single channel for passing fluid. A male connector may be referred to as a male single channel fluid connector, and a female connector may be referred to as a female single channel connector. When the male single channel fluid connector and the female single channel connector are connected, their respective single channel match each other such that a fluid tight connection or fitting is achieved with one common channel and fluid can only be passed in the connection via the common channel. No other channels are present in the connectors. The single channels are further preferably located centered in the connectors. Thus, the single channel of the male single channel fluid connector is located centered in the same connector. Further, the single channel of the female single channel fluid connector is located centered in the same connector.

The centered single channels allow rotational engagement of the connectors. Rotational engagement here generally means that while the male single channel fluid connector is inserted into the female single channel fluid connector to form a fluid tight connection, any of the engaging parts of the connectors may be rotated in relation to the other engaging part of the other connector of the connection. The engaging parts may be the hollow male portion, e.g. the inner hollow male portion, and the hollow female portion. Non-rotational engagement is also allowed in some embodiments.

BRIEF DESCRIPTION OF THE DRAWINGS

FIG. 1A shows a standard male Luer connector with a slip tip arranged on a male connector body.

FIG. 1B shows a standard female Luer connector configured to receive the male Luer connector with the slip tip in FIG. 1A, and a male Luer connector with a lock tip in FIG. 1C.

FIG. 1C shows the standard male Luer connector with the lock tip arranged on a male connector body.

FIG. 1D shows a standard female Luer connector configured to receive the male Luer connector with a lock tip in FIG. 1C, and the male Luer connector with the slip tip in FIG. 1A.

FIG. 2A shows a male connector of a second type according to one embodiment.

FIG. 2B shows a male connector of the second type according to another embodiment.

FIG. 2C shows a female connector of a second type according to one embodiment.

FIG. 2D shows a female connector of the second type according to another embodiment.

FIG. 2E shows a vertical cross-section along a center line c of the male connector of the second type in FIG. 2B.

FIG. 2F shows a vertical cross-section along a center line c of the female connector of the second type in FIG. 2D.

FIG. 4A shows a cross-section of the male connectors in FIGS. 3A and 3B according to one embodiment, but with a first structure divided in two structure parts.

FIG. 4B shows a cross-section of the female connectors of the second type in FIGS. 3D and 3E according to one embodiment, but with a second structure divided in two structure parts.

FIG. 4C shows an alternative embodiment of the male connector of FIG. 4A, where the first structure is rotated 90°.

FIG. 4D shows an alternative embodiment of the female connector of FIG. 4B, where the second structure is rotated 90°.

FIG. 4E shows a cross-section of the male connector in FIG. 3C.

FIG. 4F is a cross-section of the female connector in FIG. 3F.

DETAILED DESCRIPTION

Figure 3A:
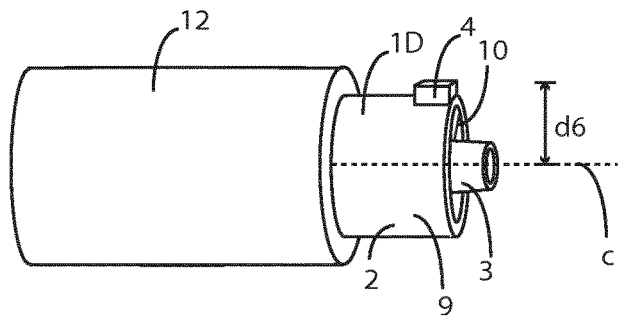
FIG. 3A shows a male connector of a second type according to one embodiment.

FIGS. 1A-1D are illustrating prior art Luer connectors that now will be explained with reference to these figures. The Luer connectors are here illustrated in isolation as male connectors and female connectors, but may instead be connected to for example a syringe barrel, a needle, a fluid line or a fluid bag. A male connector and a female connector may together be referred to as a connection or a connection system. A slip tip is here defined as a male connector that is arranged to use friction against a female connector to create a fluid tight fitting between them. A lock tip is further defined as a male connector arranged with one or several threads mating with corresponding threads on a female connector, such that a fluid tight fitting can be created between them by screwing them together. The connectors described herein may e.g. be made of plastic or metal.

FIG. 1A illustrates a male fluid connector 1A with a slip tip. The male fluid connector 1A comprises a male connector body 2 defining a hollow male portion 3. The hollow male portion 3 here has a tapered shape of a cone. According to one embodiment, the cone has a 6% taper. The hollow male portion 3 incorporates the single fluid channel of the male fluid connector 1A. The hollow male portion 3 is here attached to a hollow attachment part 12 which may be arranged to be connected to a fluid bag or fluid line. The attachment part 12 may instead be exchanged for e.g. a syringe barrel, and the hollow male portion 3 may be arranged directly to the syringe barrel. The embodiment shown in FIG. 1A may be referred to as a male fluid connector of first type 1A with slip tip.

FIG. 1B is illustrating a female fluid connector 5A according to one embodiment with a female connector body 6 defining a female hollow portion 8. The hollow female portion 8 here has a tapered shape of a cone. According to one embodiment, the cone has a 6% taper. The hollow female portion 8 incorporates the single fluid channel of the female fluid connector 5A. The female fluid connector 5A is arranged to receive the male fluid connector 1A of FIG. 1A in order to create a fluid tight connection between them. As is understood, any of the female fluid connector 5A and the male fluid connector 1A may be rotated in relation to each other while the connectors 1A, 5A are engaged, and this rotation will not compromise the engagement. The fluid tight connection is held in place by friction acting between the inside of the hollow female portion 8 of the female fluid connector 5A and the outside of the hollow male portion 3 of the male fluid connector 1A. A first flange 13 is arranged to the female connector body 6 at one end, whereby the female fluid connector 5A by means of the first flange 13 may be joined to a male fluid connector 1B with a lock tip as illustrated in FIG. 1C. At the other end of the female connector body 6, a needle, fluid line or fluid bag may be attached. A distance between a center line c of the female hollow portion 8 and an outermost side of the flange 13 is denoted d1. The embodiment shown in FIG. 1B may be referred to as a female fluid connector of first type 5A for slip tip or lock tip.

FIG. 1C illustrates a male fluid connector 1B with a lock tip. The male fluid connector 1B has a male connector body 2 defining an inner hollow male portion 3. The hollow male portion 3 here has a tapered shape of a cone. According to one embodiment, the cone has a 6% taper. The inner hollow male portion 3 incorporates the single fluid channel of the male fluid connector 1B. The male connector body 2 is further defining an outer collar 9 surrounding the hollow male portion 3. The outer collar 9 is spaced radially from the hollow male portion 3. The outer collar 9 is further internally threaded as shown by the threads 10. The first flange 13 of the female fluid connector 5A in FIG. 1B fits with the internal thread 10 of the outer collar 9 to create the fluid tight fitting when the female fluid connector 5A is screwed to the internally threaded collar 9. The threads 10 may be separated into two separate threads, such that the threads may be engaged by the first flange 13 at two different opposite locations of the inside of the collar 9. Such a construction with separated threads is referred to as a double thread. A distance between the outer side of the outer collar 9 and a center line c of the hollow male portion 3 is denoted d4. In similarity with the embodiment in FIG. 1A, the hollow male portion 3 is here illustrated attached to a hollow attachment part 12 which may be arranged to a fluid line or fluid bag. The attachment part 12 may instead be exchanged for e.g. a syringe barrel, and the hollow male portion 3 may then be arranged directly to the syringe barrel. The embodiment shown in FIG. 1C may be referred to as a male fluid connector of first type 1B with lock tip, or as a male fluid Luer lock connector. The outer collar 9 may also be attached to or integrated with the attachment part 12 or the hollow male portion 3.

FIG. 1D illustrates a female fluid connector 5B according to another embodiment comprising a female connector body 6 defining a hollow female portion 8. The embodiment shown in FIG. 1D may be referred to as a female fluid connector of first type 5B for lock tip. The hollow female portion 8 has a shape of a cylinder with an external thread 11. The hollow female portion 8 further has an internal tapered shape of a cone. According to one embodiment, the internal cone has a 6% taper. The hollow female portion 8 incorporates the single fluid channel of the female fluid connector 5B, that is, the cone constitutes the single fluid channel. The external thread 11 fits with the internal thread 10 of the outer collar 9 of the male fluid connector 1B of FIG. 1C to create a fluid tight fitting when the fluid connector 5B of FIG. 1D is screwed to the internally threaded outer collar 9. Also friction acting between the outside of the inner hollow male portion 3 and the inside of the hollow female portion 8 creates the fluid tight fitting. The external thread 11 may be separated into two separate threads as a double thread, such that the separate threads may be engaged with the male connector 1B of FIG. 1C with equally separated threads. The beginnings of the external threads 11 are then located at opposite locations of the outside of the hollow female portion 8. A distance between a center line c of the hollow female portion 8 and an outermost side of the female connector body 6 is denoted d2. Instead of an external thread 11, the hollow female portion 8 may be arranged with another structure that fits with the internal thread 10 of the male fluid connector. The female connector body 6 may be engaged with a male connector at one end, and at the other end of the female connector body 6 a needle, fluid line or fluid bag may be attached. The female connector 5B may be referred to as a female fluid Luer lock connector. The male connector of FIG. 1C and the female connector of FIG. 1D may together be referred to as a Luer lock connection.

The female and male fluid connectors in FIGS. 1A-1D are herein generally referred to as female and male fluid connectors of first type, respectively.

In FIGS. 2A-4F, connectors generally referred to as female and male fluid connectors of a second type, respectively, are illustrated and hereafter explained with reference to these figures. The female and male connectors of the second type are all single channel fluid connectors.

In FIGS. 2A and 2B male fluid connectors 1C of second types are shown. The male fluid connectors 1C each comprise the male connector body 2 defining the hollow male portion 3. The hollow male portion 3 here has a tapered shape of a cone. According to one embodiment, the cone has a 6% taper. So far this structure corresponds to the male fluid connector of the first type 1A shown in FIG. 1A. The male connector body 2 further has a first structure 4 exterior of the hollow male portion 3. In the embodiment shown in FIG. 2A, the structure 4 has a shape of an "L" with the shorter leg of the "L" arranged to a distal end of the hollow male portion 3 closest to the attachment part 12, and the longer leg of the "L" arranged lengthwise of the hollow male portion 3. The first structure 4 is here only shown with one "L", but could be divided into at least two first structure parts spaced apart around the circumference of the hollow male portion 3. The first structure parts could thus have the same shape as the shown "L", and be arranged with equidistance around the circumference of the hollow male portion 3. The number of first structure parts may be two, four or six. The first structure 4 allows rotational engagement of the male connector body 2 with a female connector of a first type 5A, 5B with a hollow female portion 8 as shown in FIG. 1B or 1D. This because a distance d3 between the underside of the longer leg of the "L" and a center line c of the hollow male portion 3 is greater than the distances d1 and d2 of the female connectors of the first type 5A, 5B. The first structure 4 has in the embodiment shown in FIG. 2A a same length along the male connector body 2 as the length of the hollow male portion 3. The structure 4 may instead of having a shape of an "L", have a shape of an "I". The shorter leg of the "L" may be removed and the "I" attached directly to the attachment part 12. The embodiment shown in FIGS. 2A and 2B may be referred to as male fluid connectors of second type with slip tip.

In the embodiment shown in FIG. 2B the first structure 4 has a shape of a collar encircling the hollow male portion 3. The first structure 4 allows rotational engagement of the male connector body 2 with the female connector of the first type 5A, 5B with a hollow female portion 8 as shown in FIGS. 1B and 1D. In the embodiments shown in FIGS. 2A and 2B also non-rotational engagement of the male connector body 2 with the female connector of the first type 5A, 5B with a hollow female portion 8 as shown in FIGS. 1B and 1D.

The hollow male portion 3 is here attached to a hollow attachment part 12 which may be arranged to be connected to a fluid bag or fluid line. The attachment part 12 may instead be exchanged with e.g. a syringe barrel, and the hollow male portion 3 may be arranged directly to the syringe barrel.

The first structure 4 of the embodiments shown in FIGS. 2A and 2B however prevents any engagement with a female connector of a second type 5C as shown in FIGS. 2C and 2D, with a hollow female portion 8 having a second structure 7 exterior of the hollow female portion 8. The first structure 4 is designed to match the second structure 7 such that engagement is prevented. This matching will be more explained in the following.

FIGS. 2C and 2D show female fluid connectors 5C of the second type according to two different embodiments. The female fluid connector 5C of the second type has a female connector body 6 defining a female hollow portion 8. The hollow female portion 8 here has a tapered shape of a cone. According to one embodiment, the cone has a 6% taper. A first flange 13 is attached to the female hollow portion 8. So far this structure corresponds to the female fluid connector of the first type 1A shown in FIG. 1B. The female connector body 6 further has a second structure 7 exterior of the female hollow portion 8 allowing rotational engagement within the female connector body 6 with a male connector of a first type 1A with a hollow male portion 3 as shown in FIGS. 1A and 1C. The second structure 7 is arranged to or attached to the hollow female portion 8 or to the fluid line connection part 14. The second structure 7 has in these embodiments a bell-like shape, but may instead have a shape of a cylinder or any other appropriate shape. The second structure 7 here further encircles the female portion 8. In other embodiments not shown, the second structure 7 may be arranged to only at least partly extend around the circumference of the female portion 8. For example, if the first structure 4 encircles the hollow male portion 3, the second structure 7 does not have to encircle the hollow female portion 8. Instead, the second structure 7 may be arranged as one or several projecting parts matching the first structure 4, projecting from the hollow female portion 8 or from the fluid line connection part 14. According to one embodiment, the second structure 7 encircles the hollow female portion 8 to at least 50%. In the embodiment shown in FIG. 2C, the second structure 7 is arranged with a flange 15. The second structure 7 is in these embodiments joined with the female hollow portion 8 at a distal end of the female connector body 6, close to a fluid line connection part 14 of the female fluid connector 5B. A circumferential space is created between the second structure 7 and the female hollow portion 8. In this space the collar 9 of the male fluid connector 1B in FIG. 1C may be accommodated. The space thus has an extension such that the outer collar 9 of the male connector 1B in FIG. 1C fits into the space. Thus, both the male connectors 1A, 1B of the first type shown in FIGS. 1A and 1C may be connected to the female connectors of the second type 5C of FIGS. 2C and 2D. However, the second structure 7 prevents any engagement with the male connector of the second type 1C with a hollow male portion 3 having the first structure 4 exterior of the hollow male portion 3 as exemplified in FIGS. 2A and 2B. The second structure 7 is thus designed to match the first structure 4 of the male connector 1C such that any engagement is prevented. The embodiments shown in FIGS. 2C and 2D may be referred to as female fluid connectors of second type 5C for slip tip.

In FIG. 2E a vertical cross-section along the center line c of the male connector of the second type 1C in FIG. 2B is shown, and in FIG. 2F a vertical cross-section along the center line c of the female connector of the second type 5C in FIG. 2D is shown. As understood from the figures, the male connector 1B and the female connector 5B cannot be engaged with each other, as the first structure 4 of the male connector 1B and the second structure 7 of the male connector 5B match. This means that the first structure 4 and the second structure 7 are arranged to the female and male connector, respectively, such that the first structure 4 and the second structure 7 are cross-sectionally overlapping at least to some extent when the connectors are aligned along the center line c, and thereby engagement is prevented. According to one embodiment, the first structure 4 and the second structure 7 are cross-sectionally overlapping irrespective of their respective degree of rotation around the center line c, when the connectors are aligned along the center line c. Thus, the first structure 4 and the second structure 7 are always overlapping when the connectors are aligned along the center line c. The match and overlap is pointed out by the longitudinal arrows between the figures.

Figure 3D:
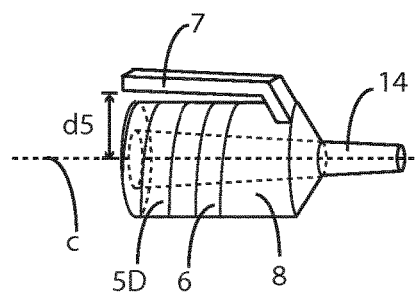
FIG. 3D shows a female connector of a second type according to one embodiment.
Figure 3B:
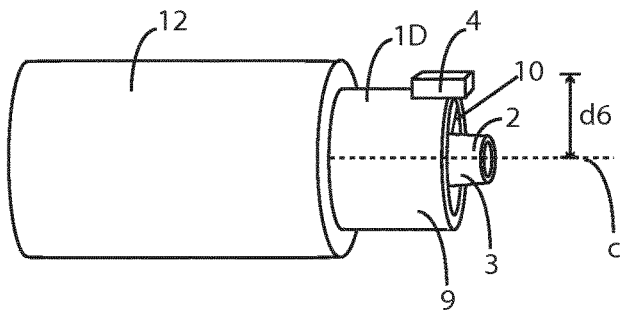
FIG. 3B shows a male connector of the second type according to another embodiment.
Figure 3E:
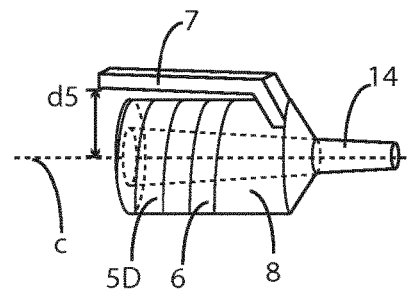
FIG. 3E shows a female connector of the second type according to another embodiment.
Figure 3C:
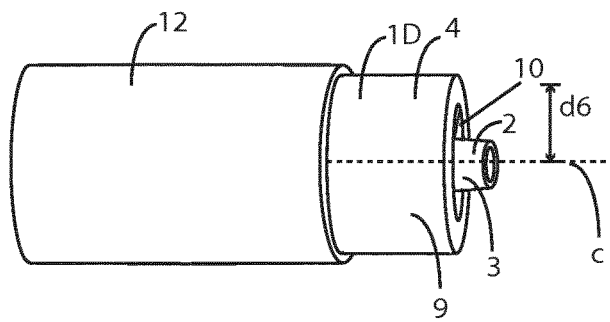
FIG. 3C shows a male connector of the second type according to a still another embodiment.

In FIGS. 3A-3C male fluid connectors of the second type 1D are shown. The male fluid connectors 1D comprise the male connector body 2 defining an inner hollow male portion 3. The inner hollow male portion 3 has a tapered shape of a cone. According to one embodiment, the cone has a 6% taper. The inner hollow male portion 3 incorporates the single fluid channel of the male fluid connector 1D. The male connector body 2 is further defining the outer collar 9 surrounding the inner hollow male portion 3. The outer collar 9 is spaced radially from the hollow male portion 3. The outer collar 9 is further internally threaded with the thread 10. The internal thread may be separated into two separate threads, such that the separate threads may mate with equally separated threads on a female connector. The beginnings of the internal threads are then located at opposite locations of the inside of the outer collar 9. So far the structures in FIGS. 3A-3C correspond to the male fluid connector of the first type 1A shown in FIG. 1C. The male connector body 2 further has the first structure 4 exterior of the hollow male portion 3. The first structure 4 is extending radially from the exterior of the outer collar 9. The first structure 4 allows rotational engagement of the male connector body 2 with a female connector of a first type 5A with a hollow female portion 8, as shown in FIGS. 1B and 1D. This because the first structure 4 is arranged to the exterior of the outer collar 9, meanwhile the female connector of the first type 5A is fitted in a space created between the hollow male portion 3 and the collar 9. The embodiments shown in FIGS. 3A-3C may be referred to as male fluid connectors of second type 1D with lock tip.

In the embodiment shown in FIG. 3A, the first structure 4 has a cubic or boxlike shape, but may have another kind of shape such as rectangular, cylindrical, spherical etc. The first structure 4 is arranged to the outside of the collar 9, close to or adjacent a front edge of the collar 9. The first structure 4 may be divided into at least two first structure parts spaced apart around the circumference of the collar 9. The first structure parts could thus have the same shape as the shown form of FIG. 3A, and be arranged with equidistance around the circumference of the collar 9. The number of first structure parts may be two, four or six. The first structure 4 may further according to another embodiment extend at least partly around the circumference of the hollow male portion 3.

In the embodiment shown in FIG. 3B, the first structure 4 differs from the embodiment shown in FIG. 3A in that the first structure 4 extends beyond the collar 9 in a direction of engagement with the female connector 5B. Otherwise the characteristics of the embodiment in FIG. 3A may be the same as the characteristics of the embodiment of FIG. 3B.

In the embodiment shown in FIG. 3C, the first structure 4 extends around the whole circumference of the hollow male portion 3. The first structure 4 here has a shape of a layer of a first material. The layer is arranged to the outer collar 9 such that the thickness of the outer collar 9 of the male fluid connector 1C of FIG. 3C together with the thickness of the layer becomes greater than the thickness of the outer collar 9 of the male fluid connector 1A of FIG. 1C. According to one embodiment, the first structure 4 and the collar 9 are made in one piece.

The hollow male portion 3 is here attached to a hollow attachment part 12 which may be arranged to be connected to a fluid bag or fluid line. The attachment part 12 may instead be exchanged for e.g. a syringe barrel, and the hollow male portion 3 may be arranged directly to the syringe barrel.

Figure 3F:
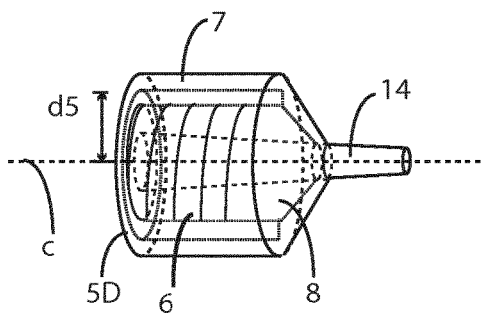
FIG. 3F shows a female connector of the second type according to a still another embodiment.

The first structure 4 prevents engagement with a female connector of a second type 5C with a hollow female portion 8 having a second structure 7 exterior of the hollow portion as illustrated in FIGS. 3D-3F. The first structure 4 is thus designed to match the second structure 7 such that engagement is prevented.

In FIGS. 3D-3F the female fluid connectors of the second type 5D are shown. The female fluid connectors 5D each comprise the female connector body 6 defining a female hollow portion 8. The female hollow portion 8 here has an outer shape of a cylinder with an external thread. The external thread may be separated into two separate threads into a double thread, such that the separate threads may be engaged with a female connector of FIGS. 3A-3C with equally separated threads. The beginnings of the external threads are then located at opposite locations of the outside of the cylinder. The female hollow portion 8 further has an internal tapered shape of a cone. According to one embodiment, the internal cone has a 6% taper. The female hollow portion 8 incorporates the single fluid channel of the female fluid connector 5D, that is, the cone constitutes the single fluid channel. So far the structures in FIG. 3D-3F correspond to the female fluid connector of the first type 5B shown in FIG. 1D. The female connector body 6 further has the second structure 7 exterior of the female hollow portion 8. In the embodiment shown in FIGS. 3D and 3E the second structure 7 has a shape of a tilted "L" or a handle attached or joined to the female hollow portion 8 at a distal end of the female connector body 6, close to a fluid line connection part 14 of the female fluid connector 5C. The longest leg of the "L" is arranged lengthwise of the female hollow portion 8.

The second structure 7 is here only shown with one "L", but may be divided into at least two second structure parts spaced apart around the circumference of the female hollow portion 8. The second structure parts could thus have the same shape as the shown "L", and be arranged at equidistance around the circumference of the female hollow portion 8. The number of second structure parts may be two, four or six. The second structure 7 allows rotational engagement of the female connector body 6 with a male connector of a first type 1A, 1B with a hollow male portion 3 as shown in FIGS. 1A and 1C. This because a distance d5 between the lower side of the long leg of the "L" and a center line c of the hollow female portion 8 is greater than a distance d4 of the male connectors of the first type 1B of FIG. 1C. The embodiments shown in FIGS. 3D-3F may be referred to as female fluid connectors of second type for lock tip.

In the embodiment shown in FIG. 3E the second structure 7 extends beyond the female hollow portion 8 in a direction of engagement with a male connector. Otherwise the embodiment in FIG. 3E may have the same characteristics as the embodiment in FIG. 3D.

In the embodiment shown in FIG. 3F the second structure 7 has a shape of a cylinder encircling the female hollow portion 8. The second structure 7 may here also be referred to as a sleeve or collar. A space is then created between the second structure 7 and the female hollow portion 8 into which the hollow male portion 3 of the male connector of a first type 1B as shown in FIG. 1C may be inserted. The second structure 7 here has a same length along the female connector body 6 as the length of the female hollow portion 8.

The second structure 7 however prevents any engagement with the male connectors of the second type 1D with the hollow male portion 3 having a first structure 4 exterior of the hollow male portion 3, shown in FIGS. 3A-3C. The second structure 7 is designed to match the first structure 4 such that engagement is prevented. More specifically, the first structure 4 is designed to prevent rotational engagement of the male connector 1D to the female connector of the second type 5D. Further, the second structure 7 is designed to prevent any engagement, e.g. rotational engagement, of the female connector 5D to the male connector of the second type 1D.

Figure 3G:
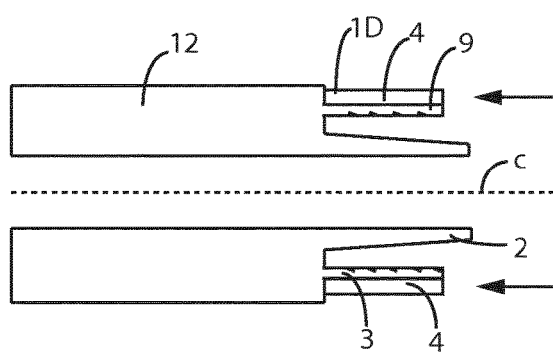
FIG. 3G shows a vertical cross-section along a center line c of the male connector of the second type in FIG. 3C.
Figure 3H:
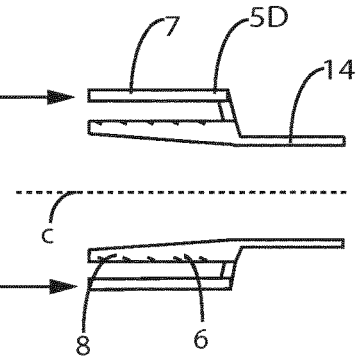
FIG. 3H shows a vertical cross-section along a center line c of the female connector of the second type in FIG. 3F.

In FIG. 3G a vertical cross-section along the center line c of the male connector of the second type 1D in FIG. 3C is shown, and in FIG. 3H a vertical cross-section along the center line c of the female connector of the second type 5D in FIG. 3F is shown. As understood from the figures, the male connector 1D and the female connector 5D cannot be engaged with each other, as the first structure 4 of the male connector 1C and the second structure 7 of the male connector 5C match. This means that the first structure 4 and the second structure 7 are arranged to the female and male connector, respectively, such that the first structure 4 and the second structure 7 are cross-sectionally overlapping at least to some extent when the connectors are aligned along the center line c, and thereby prevents engagement. According to one embodiment, the first structure 4 and the second structure 7 are cross-sectionally overlapping irrespective of their respective degree of rotation around the center line c, when the connectors are aligned along the center line c. Thus, the first structure 4 and the second structure 7 are always overlapping when the connectors are aligned along the center line c. The match and overlap is pointed out by the longitudinal arrows between the figures.

FIGS. 4A and 4B are illustrating vertical cross sections of embodiments previously described. FIG. 4A shows a vertical cross section of the second type male connector 1D with the first structure 4 divided into two structure parts located at opposite positions around the internally threaded collar 9. The internal thread 10 is here separated into two separate threads, such that the separate threads may be engaged with a female connector with equally separated threads. The beginnings of the internal threads 10 are then located at opposite locations of the inside of the collar 9, as illustrated in the figure. FIG. 4B shows a vertical cross section of the second type female connector 5D with the second structure 7 divided into two structure parts located radially spaced from and at opposite positions around the externally threaded female hollow portion 8. As understood from the figures, the male connector 1D and the female connector 5D cannot be engaged with each other, as the first structure 4 of the male connector 1D and the second structure 7 of the male connector 5D match, as has been previously described. The match and overlap is pointed out by the longitudinal arrows between the figures. Also the internal threads 10 of the collar 9 and the external threads 11 of the threaded female hollow portion 8 are matched against each other, such that the beginnings of the threads on respective part are mirrored. Further, the beginnings of the threads 10 on the collar 9 are located in a relation to the first structure 4, and the beginnings of the threads 11 of the threaded female hollow portion 8 are located in a relation to the second structure 7, such that when the beginnings of the threads of the collar 9 are aligned with the beginnings of the threads of the female hollow portion 8, the first structure 4 and the second structure 7 are overlapping and prevents rotational engagement between the male connector 1D and female connector 5D. The threads could however possible be engaged also if one of the parts is rotated 180°, but as the structures 4, 7 are comprised of two structure parts located at opposite positions, the structures would still overlap and rotational engagement can be prevented.

FIGS. 4C and 4D are illustrating cross sections of similar embodiments as described with reference to FIGS. 4A and 4B, with the difference that the first structure 4 in FIG. 4C is rotated 90° about the collar 9, and the second structure 7 in FIG. 4B is rotated correspondently 90° about the female hollow portion 8. The threads 10, 11 and thread openings are still at the same positions as in FIGS. 4A and 4B as illustrated in the figures. As the parts are double threaded, one of the parts may be rotated 180° to supposedly engage with the other part, but as the structures 4, 7 each has two structure parts located at opposite positions, the structures would still overlap and engagement can be prevented.

In FIG. 4E a cross-section of the male fluid connector 1D of FIG. 3C is illustrated. In the figure the first structure 4, here the collar, is encircling the hollow male portion 3. In FIG. 4F a cross-section of the female fluid connector 5D of FIG. 3F is illustrated. In the figure the second structure 7, the cylinder, is encircling the female hollow portion 8. The embodiments are each concentrically arranged. As can be seen from the figures, the hollow male portion 3 fits within the female hollow portion 8. However, the first structure 4 has an outer radius that is equal to or close to equal to the outer radius of the second structure 7, and thereby the male fluid connector of FIG. 3C cannot be engaged with the female fluid connector of FIG. 3F. The male fluid connector 1D and the female fluid connector 5D may be double threaded.

The male fluid connector 1C, 1D may according to one embodiment be made in one piece. The female fluid connector 5C, 5B may according to one embodiment be made in one piece.

The male fluid connector 1C, 1D of the second type and the female fluid connector 5C, 5D of the second type may be comprised in a fluid connection system.

Figure 5A:
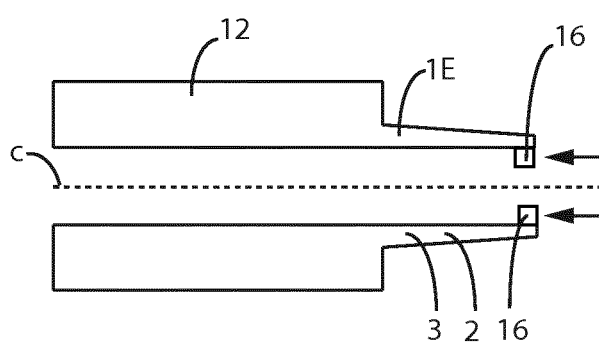
FIG. 5A shows a cross-section of a male connector of a third type according to one embodiment.
Figure 5B:
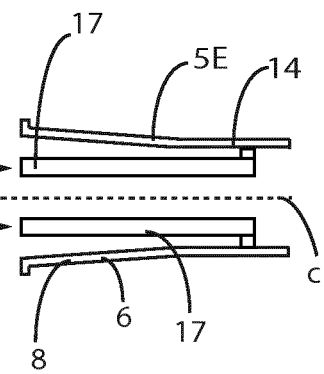
FIG. 5B shows a cross-section of a female connector of a third type according to one embodiment.
Figure 5C:
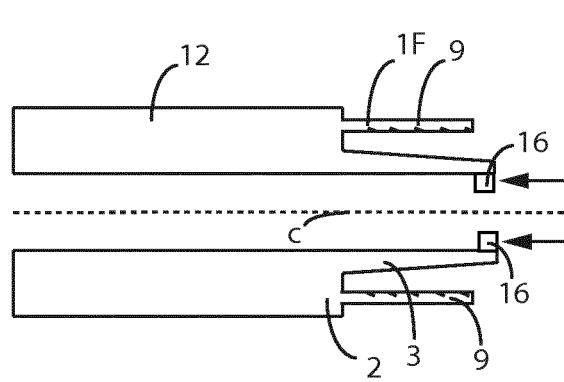
FIG. 5C shows a cross-section of a male connector of the third type according to another embodiment.

The disclosure also relates to male connectors of a third type 1E, 1F having a first structure interior of the hollow male portion, as illustrated in FIGS. 5A and 5C. In FIGS. 5A and 5C cross-sections of embodiments of the male connector 1E are illustrated, and will now be explained with reference to these figures. The male fluid connector 1E, 1F comprises a male connector body 2 defining a hollow male portion 3. The hollow male portion 3 incorporates the single fluid channel of the male fluid connector 1E. The male connector body 2 has a third structure 16 interior of the hollow male portion 3 allowing rotational engagement of the male connector body 2 with a female connector of a first type 5A with a hollow female portion 8, but preventing any engagement with a female connector of a third type 5E, 5F with a hollow female portion 8 having a fourth structure 17 interior of the hollow female portion 8. The female hollow portion 8 incorporates the single fluid channel of the female fluid connector 5E. The fourth structure 17 thus extends inside the single fluid channel. The third structure 16 is designed to match the fourth structure 17 such that any engagement is prevented. The embodiment of FIG. 5A may be referred to as a male fluid connector of third type 1E with slip fit. The embodiment of FIG. 5C may be referred to as a male fluid connector of third type 1F with lock tip. According to one embodiment, the third structure 16 has a shape of a layer of a first material. The third structure 16 may extend beyond the hollow male portion 3 in a direction of engagement with the female connector 5E, 5F. The third structure 16 may extend at least partly around the circumference of the inside of the hollow male portion 3. The third structure 16 may be divided into at least two third structure parts spaced apart along the circumference of the inside of the hollow male portion 3. The third structure 16 may extend along the whole circumference of the inside of the hollow male portion 3. The third structure 16 may be designed to prevent rotational engagement of the male connector 1E to the female connector of the third type 5E. The male connector 1E, 1F may be made in one piece. According to one embodiment, the hollow male portion 3 is an inner hollow male portion, and the male connector body 2 is further defining an outer collar 9 surrounding the hollow male portion 3 and spaced radially therefrom, the outer collar 9 is internally threaded 10, wherein the third structure 16 is extending radially from the interior of the hollow male portion 3. According to another embodiment, the third structure 16 is designed such that the third structure 16 and the fourth structure 17 radially and circumferentially at least partly overlap when a center line c of the female connector of the third type 5E, 5F and the male connector 1E, 1F, respectively, are aligned and a thread opening of the internal thread 10 of the male connector of the third type 1E, 1F is aligned with a thread start of the female connector of the third type 5E, 5F. The hollow male portion 3 may have a tapered shape.

Figure 5D:
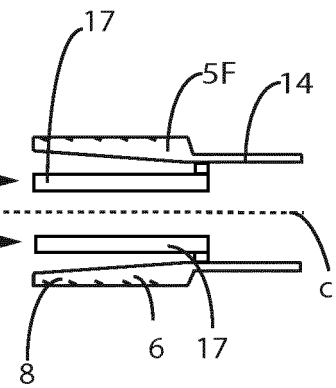
FIG. 5D shows a cross-section of a female connector of the third type according to another embodiment.

In FIGS. 5B and 5D cross-sections of embodiments of the female connector of the third type 5E, 5F are illustrated, and will now be explained with reference to these figures.

The female fluid connector 5E, 5F here comprises a female connector body 6 defining a female hollow portion 8. The female hollow portion 8 incorporates the single fluid channel of the female fluid connector 5E. The female connector body 6 has a fourth structure 17 interior of the female hollow portion 8 allowing rotational engagement within the female connector body 6 with a male connector of a first type 1A, 1B with a hollow male portion 3, but preventing any engagement with a male connector of a third type 1E, 1F with a hollow male portion 3 having a third structure 16 interior of the hollow male portion 3, thus into the single fluid channel, and the fourth structure 17 is designed to match the third structure 16 such that any engagement is prevented. The fourth structure 17 may at least partly extend around the circumference of the inside of the female portion 8. The fourth structure 17 may extend beyond the female hollow portion 8 in a direction of engagement. The fourth structure 17 may be divided into at least two fourth structure parts spaced apart along the circumference of the inside of the female hollow portion 8. The fourth structure 17 may have a shape of a sleeve. The fourth structure 17 may be designed to prevent rotational engagement of the female connector 5E, 5F to the male connector of the third type 1E, 1F. The female connector 5E, 5F may be made in one piece. The female hollow portion 8 may have an external thread 11. According to one embodiment, the fourth structure 17 is designed such that the fourth structure 17 and the third structure 16 of the male connector of the third type 1E, 1F radially and circumferentially at least partly overlap when a center line c of the male connector of the third type 1E, 1F and the female connector 5E, 5F respectively, are aligned and a thread start of the external thread 11 of the female connector 5E, 5F is aligned with a thread opening of a thread of the male connector of the third type 1E, 1F. The female hollow portion 8 may have a tapered shape. The embodiment of FIG. 5B may be referred to as a female fluid connector of third type 5E for slip fit. The embodiment of FIG. 5D may be referred to as a female fluid connector of third type 5F for lock tip.

The fluid connection system may according to one embodiment comprise the above described male connector of the third type 1E, 1F and the female connector 5E, 5F. The fluid connection system may thus comprise the male fluid connector 1E, 1F with a male connector body 2 defining a hollow male portion 3 and a female fluid connector 5E, 5F with a female connector body 6 defining a hollow female portion 8. The male connector 1E, 1F is thus of a third type male connector 1E, 1F wherein the male connector body 2 has the third structure 16 interior of the hollow male portion 3 allowing engagement of the male connector body 2 with a female connector of a fourth type 5E, 5F with a hollow female portion 8. The female connector 5E, 5F is then of a third type female connector 5E, 5F wherein the female connector body 6 has the fourth structure 17 interior of the hollow female portion 8 allowing rotational engagement within the female connector body 6 with a first type of male connector 1A, 1B with a hollow male portion 3, but preventing any engagement with a third type of male connector 1E, 1F. The third structure 16 of the third type male connector 1E, 1F is here designed to match the fourth structure 17 of the third type female connector 5E, 5F such that any engagement is prevented between the third type male connector 1E, 1F and the third type female connector 5E, 5F.

In the fluid connection system, the third structure 16 may have a shape of a layer of a first material. The third structure 16 may extend beyond the hollow male portion 3 in a direction of engagement with the female connector 5E, 5F. The third structure 16 may extend at least partly along the circumference of the inside of the hollow male portion 3. The third structure 16 may be divided into at least two third structure parts spaced apart along the inside of the circumference of the hollow male portion 3. The third structure 16 may extend around the whole circumference of the inside of the hollow male portion 3. The male connector 1E, 1F may be made in one piece.

In the fluid connection system, the fourth structure 17 at least partly extends around the circumference of the female hollow portion 8. The fourth structure 17 may extend beyond the female hollow portion 8 in a direction of engagement. The fourth structure 17 may be divided into at least two second structure parts spaced apart around the circumference of the female hollow portion 8. The fourth structure 17 may have a shape of a sleeve. The fourth structure 17 may have a same length along the female connector body 6 as the length of the female hollow portion 8. The female connector 5E, 5F may be made in one piece. According to one embodiment, the hollow male portion 3 of the third type male connector 1E, 1F is an inner hollow male portion, and the male connector body 2 is further defining an outer collar 9 surrounding the hollow male portion 3 and spaced radially therefrom. The outer collar 9 may be internally threaded 10, and the third structure 16 may extend radially from the interior of the hollow male portion 3, and the female hollow portion 8 of the third type female connector 5F may have an external thread 11. According to another embodiment, the third structure 16 and the fourth structure 17 are designed such that the third structure 16 and the fourth structure 17 radially and circumferentially at least partly overlap when a center line c of the second type male connector 1F and the second type female connector 5F, respectively, are aligned and a thread opening of the internal thread 10 of the second type male connector 1F is aligned with a thread start of the external thread 11 of the second type female connector 5F.

Figures 6A, 6B:
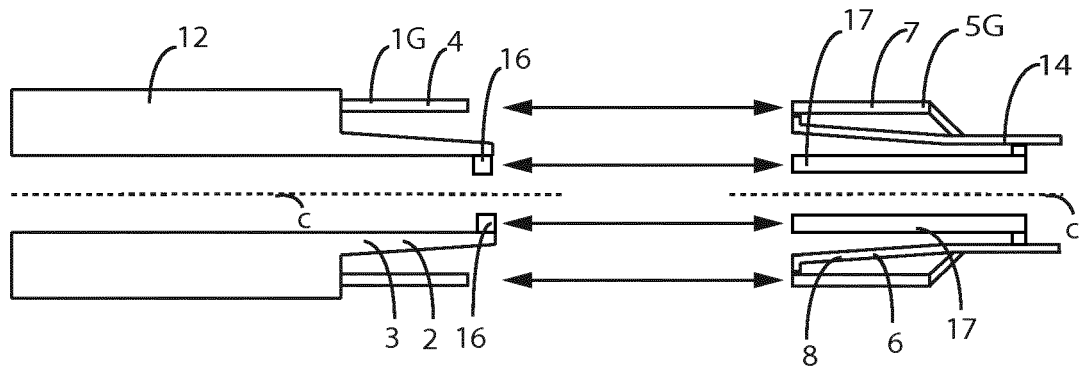
FIG. 6A shows a cross-section of a male connector of a fourth type according to one embodiment.
FIG. 6B shows a cross-section of a female connector of a fourth type according to one embodiment.
Figures 6C, 6D:
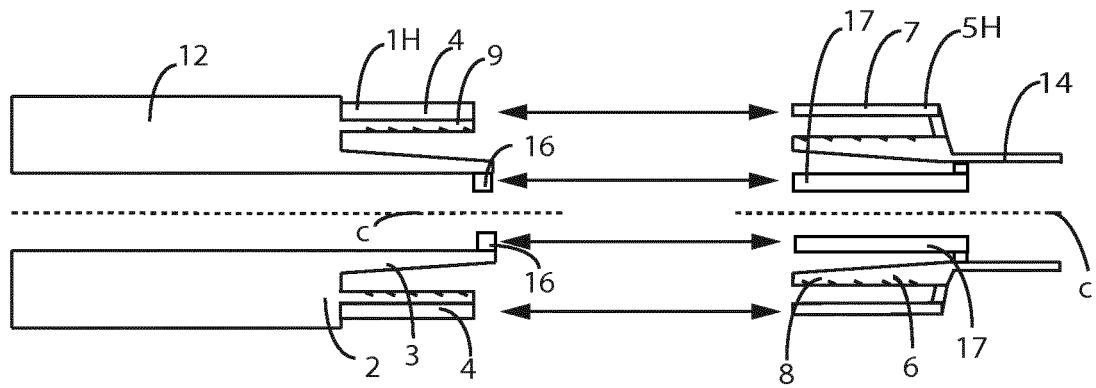
FIG. 6C shows a cross-section of a male connector of a fourth type according to another embodiment.
FIG. 6D shows a cross-section of a female connector of a fourth type according to another embodiment.

The disclosure also relates to combinations of the above described embodiments, which will now be described with reference to FIGS. 6A to 6D. In FIGS. 6A and 6C male connectors of a fourth type 1G, 1H are illustrated in cross-section. This fourth type 1G, 1H both has an external first structure 4 and an internal third structure 16. In FIGS. 6B and 6D female connectors of a fourth type 5G, 5H is illustrated in cross-section. This fourth type 5G, 5H both has an external second structure 7 and an internal fourth structure 17. These structures may be any of the above described structures, as long as the first structure 4 and the second structure 7 match, and the third structure 16 and the fourth structure 17 match as has been previously described. For example, the first structure 4 of FIG. 6A may be arranged as illustrated and described with reference to FIG. 2E, and the second structure 7 of FIG. 6B may be arranged as illustrated and described with reference to FIG. 2F. Further, the third structure 16 of FIG. 6A may be arranged as illustrated and described with reference to FIG. 5A, and the fourth structure 17 of FIG. 6B may be arranged as illustrated and described with reference to FIG. 5B. Also, the first structure 4 of FIG. 6C may be arranged as illustrated and described with reference to FIG. 3G, and the second structure 7 of FIG. 6D may be arranged as illustrated and described with reference to FIG. 3H. Further, the third structure 16 of FIG. 6C may be arranged as illustrated and described with reference to FIG. 5C, and the fourth structure 17 of FIG. 6B may be arranged as illustrated and described with reference to FIG. 5D. The embodiment shown in FIG. 6A may be referred to as a male fluid connector of fourth type 1G with slip tip. The embodiment shown in FIG. 6B may be referred to as a female fluid connector of fourth type 5G for slip tip. The embodiment shown in FIG. 6C may be referred to as a male fluid connector of fourth type 1H with lock tip. The embodiment shown in FIG. 6D may be referred to as a female fluid connector of fourth type 5G for lock tip.

In FIGS. 5A, 5C, 6A and 6C the hollow male portion 3 is attached to a hollow attachment part 12 which may be arranged to be connected to a fluid bag or fluid line. The attachment part 12 may instead be exchanged for e.g. a syringe barrel, and the hollow male portion 3 may be arranged directly to the syringe barrel.

Figure 7:
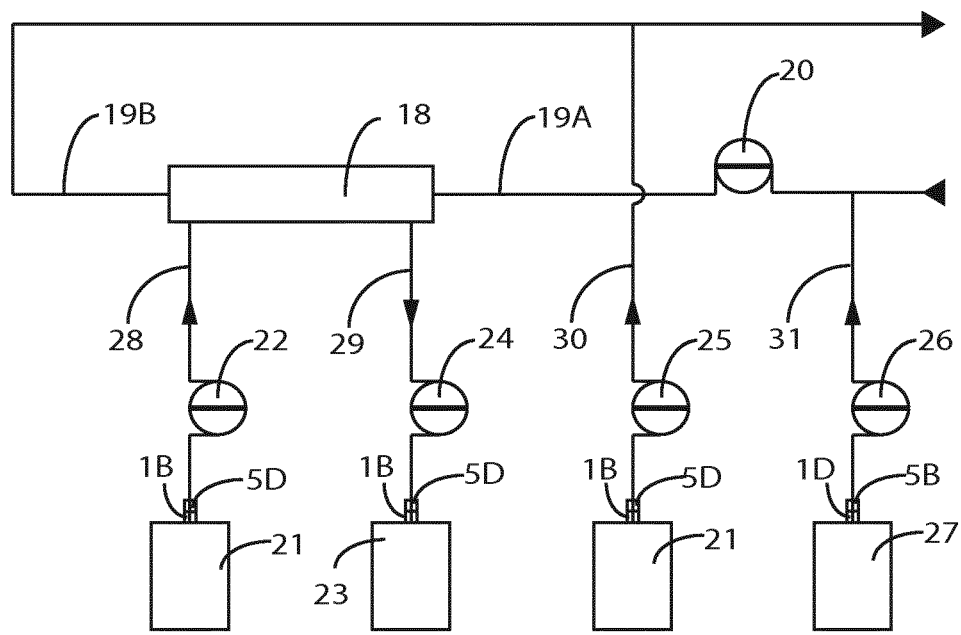
FIG. 7 shows a fluid connection system according to one embodiment applied to a dialysis system to remove the possibility of erroneously connecting a bag with citrate solution to any other fluid line of the system.

In FIG. 7 the fluid connection system according to one embodiment is applied to a dialysis system. The dialysis system is here only shown in part, and comprises a blood treatment unit 18 and a blood line 19A, 19B. The blood line 19A, 19B defines an arterial line 19A connecting a blood bag or patient (not shown) with the blood treatment unit 18 for withdrawal of blood from the blood bag or patient into the blood treatment unit 18 for treatment of the blood. The blood line 19A, 19B further defines a venous line 19B connecting the blood treatment unit 18 with a collection bag or a patient for returning of the treated blood to the collection bag or patient. A blood pump 20 arranged to the arterial line 19A pumps the blood in a direction indicated by the arrows. The dialysis system further comprises a dialysis fluid line 28 connecting a dialysis fluid bag 21 with the blood treatment unit for infusion of dialysis fluid to the blood treatment unit 18. The dialysis fluid line 28 is arranged to a dialysis fluid pump 22 that is arranged to pump the dialysis fluid into the blood treatment unit 18. The dialysis system further comprises an effluent fluid line 29 connecting the blood treatment unit 18 with an effluent fluid bag 23. The effluent fluid line 29 is arranged to an effluent pump 24 that is arranged to pump effluent fluid from the blood treatment unit 18 to the effluent fluid bag 23. The dialysis system further comprises a post replacement fluid line 30 connecting a replacement fluid bag 21 with the venous line 19B of the blood line 19A, 19B. The post replacement fluid line 30 is arranged to a replacement pump 25 that is arranged to pump replacement fluid into the venous line 19B of the blood line 19A, 19B. The dialysis system also comprises an infusion fluid line 31 connecting an infusion or anticoagulant fluid bag 27 with the arterial line 19A of the blood line 19A, 19B. The infusion fluid line 31 is arranged to an infusion pump 26 that is arranged to pump infusion or anticoagulant fluid into the arterial line 19A of the blood line 19A, 19B. The dialysis system may further include an infusion device (not shown), such as a syringe pump with a syringe, arranged for infusion of a fluid such as Calcium to the venous line 19B downstream the connection of the post replacement fluid line 30 to the venous line 19B, eventually via a fluid line arranged between the syringe and the venous line (not shown).

The infusion or anticoagulant fluid bag 27 may comprise a citrate solution that should not be infused into the blood treatment unit 18, or into the venous line 19B of the blood line 19A, 19B. The infusion or anticoagulant fluid bag 27 is therefore arranged with a male fluid connector of the second type 1D. The infusion fluid line 31 is arranged with an ordinary female fluid connector of the first type 5B. Thus, the infusion or anticoagulant fluid bag 27 may be arranged to the infusion fluid line 31 by connecting the male fluid connector of the second type 1D to the female fluid connector of the first type 5B.

To avoid infusing citrate solution into the blood treatment unit 18 by misconnection, the dialysis fluid line 28 is arranged with a female fluid connector of the second type 5D. As the infusion or anticoagulant fluid bag 27 is arranged with a male fluid connector of the second type 1D, the infusion or anticoagulant fluid bag 27 cannot be connected to the female fluid connector of the second type 5D on the dialysis fluid line 28, whereby any erroneous connection can be avoided.

To avoid infusing citrate solution into the venous line 19B of the blood line 19A, 19B, the post replacement fluid line 30 is arranged with a female fluid connector of the second type 5D. As the infusion or anticoagulant fluid bag 27 is arranged with a male fluid connector of the second type 1D, the infusion or anticoagulant fluid bag 27 cannot be connected to the female fluid connector of the second type 5D on the post replacement fluid line 30 whereby any erroneous connection can be avoided.

To avoid any misconnection of citrate to the effluent fluid line 29, also the effluent fluid line 29 is arranged with a female connector of the second type 5D. The effluent fluid line 29 may instead be arranged with an ordinary female connector of the first type 5B, as there is a low risk for infusion of citrate solution into the blood line 19 if the infusion or anticoagulant fluid bag 27 would erroneously be connected to the effluent fluid line 29.

Thus, the infusion or anticoagulant fluid bag 27 may be arranged to the infusion fluid line 31 and in some embodiments to the effluent fluid line 29, but not to the dialysis fluid line 28 or to the post replacement fluid line 30. As the connectors on the dialysis fluid bag 21, the effluent fluid bag 23 and the post replacement fluid bag 21 may be ordinary male fluid connectors of first type 1B, costs can be kept low.

Various other combinations of the herein described connectors may be applied in the above described system.

Figure 8:
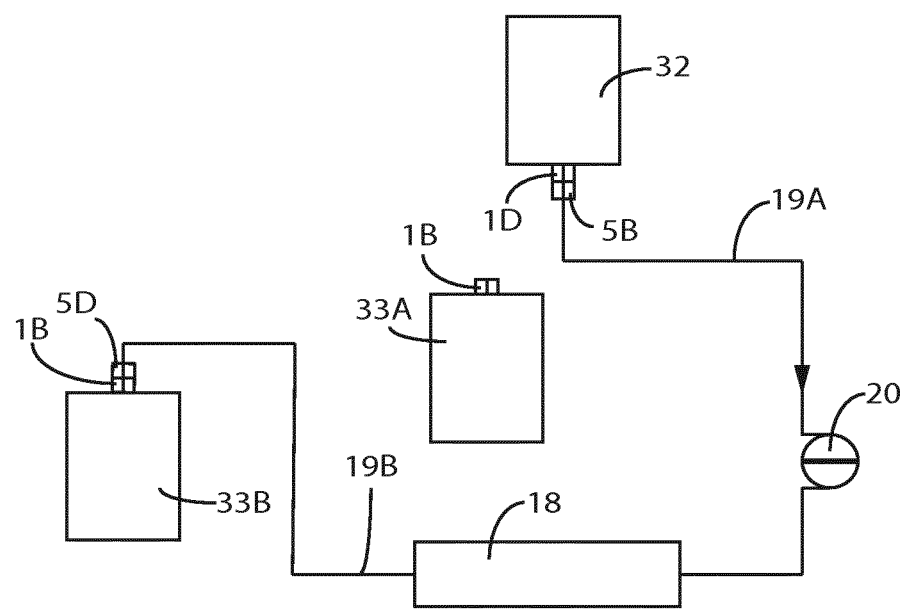
FIG. 8 shows a fluid connection system according to one embodiment applied to a dialysis system to remove the possibility of erroneously connecting a venous blood line to a fluid bag at a rinse back procedure.

In FIG. 8 the fluid connection system according to another embodiment is applied to another dialysis system. The dialysis system comprises a blood treatment unit 18 and a blood line 19A, 19B. The blood line 19A, 19B defines an arterial line 19A that may connect a blood bag 33A or patient (not shown) with the blood treatment unit 18 for withdrawal of blood from the blood bag 33A or patient into the blood treatment unit 18 for treatment of the blood. The blood line 19A, 19B further defines a venous line 19B connecting the blood treatment unit 18 with a collection bag 33B or the patient (not shown) for returning of the treated blood to the collection bag 33B or patient. A blood pump 20 arranged to the arterial line 19A pumps the blood in a direction indicated by the arrow.

In order to perform a rinse-back procedure the arterial line 19A should be disconnected from the blood bag 33A and attached to a fluid bag or fluid delivery system 32, as illustrated in the FIG. 8. The fluid from the fluid bag or fluid delivery system 32, e.g. a saline solution, may then be pumped with the blood pump 20 into the blood line 19A, 19B until the remaining blood in the blood line 19A, 19B has been returned to the collection bag 33B or patient. If instead the venous line 19B of the blood line 19A, 19B erroneously was connected to the fluid bag or fluid delivery system 32 and the arterial line 19A of the blood line 19A, 19B was still connected to the blood bag 33A or patient, the blood pump 20 may when activated pump blood from the blood bag 33A or patient to the fluid bag or fluid delivery system 32.

To avoid this scenario, the venous line 19B of the blood line 19A, 19B has been arranged with a female fluid connector of the second type 5D, and the fluid bag or fluid delivery system 32 has been arranged with a male fluid connector of the second type 1D. Thereby the venous line 19B of the blood line 19A, 19B cannot be connected to the fluid bag or fluid delivery system 32. The collection bag 33B is arranged with an ordinary male fluid connector of the first type 1B. The female fluid connector of the second type 5D on the venous line 19B of the blood line 19A, 19B may then still be connected to the male fluid connector of the first type 1B on the collection bag 33B. The blood bag 33A is also arranged with an ordinary male fluid connector of the first type 1B. The arterial line 19A of the blood line 19A, 19B is arranged with an ordinary female fluid connector of the first type 5B. The ordinary female fluid connector of the first type 5B of the arterial line 19A of the blood line 19A, 19B may thus be connected either to the ordinary male fluid connector of the first type 1B of the blood bag 33A, or to the male fluid connector of the second type 1D of the fluid bag or fluid delivery system 32. Instead of having a blood bag 33A and a collection bag 33B, an inflow needle and outflow needle to and from a patient may be used.

The dialysis systems here shown are simplified for clarity and may comprise several other devices such as another blood pump, a drip chamber, detection devices, control units etc.

Various modifications to the above described systems may be made. For example, instead of the male fluid connector of the second type 1D, a male fluid connector of the third or fourth type 1F, 1H may be used. Also, instead of a female connector of a second type 5D, a female connector of a third or fourth type 5F, 5H may be used. As understood, the male and female fluid connectors thus have to have corresponding matching structures. Further, it has been described that the female fluid connector of the second, third or fourth type is arranged on a certain device, and the male fluid connector of the second, third or fourth type is arranged on another device. The female fluid connector of the second, third or fourth type and the male fluid connector of the second, third or fourth type may however switch place with each other. Other connectors that are affected by the switch also have to be switched accordingly such that the compatibility of the system remains.

Various other applications for the fluid connector system are possible. For example may a double needle set-up and its connecting arterial and venous lines be arranged with a fluid connection system as disclosed herein such that there is no risk of attaching an arterial line and a venous line of a blood line to the double needle in an incorrect way. A further application of the fluid connection system is to avoid non-compatible fluid paths to be connected and the fluids mixed.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A male single channel fluid connector for a medical application, the male single channel fluid connector comprising:
a male connector body defining a hollow male portion, wherein the male connector body has a first structure exterior of the hollow male portion allowing rotational engagement of the male connector body with a female single channel fluid connector of a first type that is a female luer connector with a hollow female portion in order to form a fluid tight connection, but preventing any engagement with a female single channel fluid connector of a second type with a hollow female portion corresponding to the hollow female portion of the female single channel fluid connector of the first type, the female single channel fluid connector of the second type also having a second structure exterior of the hollow female portion, wherein the first structure is constructed and arranged to at least partially cross-sectionally overlap the second structure when the male single channel fluid connector and the female single channel fluid connector of the second type are aligned along a common center line such that any engagement is prevented.

2. The male single channel fluid connector according to claim 1, wherein the rotational engagement includes rotating at least one of the hollow male portion and the hollow female portion of the female single channel fluid connector of the first type in relation to each other, while inserting the hollow male portion inside the hollow female portion in order to create the fluid tight connection.

3. The male single channel fluid connector according to claim 1, wherein the first structure extends around the whole circumference of the hollow male portion.

4. The male single channel fluid connector according to claim 1, wherein the hollow male portion is an inner hollow male portion, and the male connector body is defining an outer collar surrounding the hollow male portion and spaced radially therefrom, the outer collar is internally threaded, wherein the first structure is extending radially from the exterior of the outer collar.

5. The male single channel fluid connector according to claim 4, wherein the first structure is constructed and arranged such that the first structure and the second structure radially and circumferentially at least partly overlap when a center line of the female connector of the second type and the male connector, respectively, are aligned and a thread opening of the internal thread of the male connector is aligned with a thread start of an internal thread of the female connector of the second type.

6. The male single channel fluid connector according to claim 1, wherein the hollow male portion has a tapered shape.

7. A female single channel fluid connector for a medical application, the female single channel fluid connector comprising:
a female connector body defining a female hollow portion, wherein the female connector body has a second structure having a shape of a sleeve, exterior of the female hollow portion allowing rotational engagement within the female connector body with a male single channel fluid connector of a first type that is a male luer connector with a hollow male portion in order to form a fluid tight connection, but preventing engagement with a male single channel connector of a second type with a second hollow male portion having a first structure exterior of the second hollow male portion, wherein the second structure is constructed and arranged to match the first structure such that any engagement is prevented.

8. The female single channel fluid connector according to claim 7, wherein the rotational engagement includes rotating at least one of the hollow female portion and the hollow male portion of the male single channel fluid connector of the first type in relation to each other, while inserting the hollow male portion inside the hollow female portion in order to create the fluid tight connection.

9. The female single channel fluid connector according to claim 7, wherein the female hollow portion has an external thread.

10. The female single channel fluid connector according to claim 9, wherein the second structure is constructed and arranged such that the second structure and the first structure of the male single channel fluid connector of the second type radially and circumferentially at least partly overlap when a center line of the male single channel fluid connector of the second type and the female single channel fluid connector, respectively, are aligned and a thread start of the external thread of the female single channel fluid connector is aligned with a thread opening of an internal thread of the male connector of the second type.

11. A fluid connection system for a medical application, the fluid connection system comprising:
a male single channel fluid connector of a first type that is a male luer connector with a first male connector body defining a first hollow male portion;
a female single channel fluid connector of a first type that is a female luer connector with a first female connector body defining a first hollow female portion;
a male single channel fluid connector of a second type with a second male connector body having a first structure exterior of a second hollow male portion corresponding to the first hollow male portion of the male single channel fluid connector of the first type, the first structure allowing rotational engagement of the male connector body with the female fluid connector of the first type with the first hollow female portion in order to form a fluid tight connection;
a female single channel fluid connector of a second type with a second female connector body having a second structure exterior of a second hollow female portion allowing rotational engagement within the second female connector body with the first type of male single channel fluid connector with the first hollow male portion in order to form a fluid tight connection, but preventing any engagement with the second type of male single channel fluid connector with the first structure, the second hollow female portion corresponding to the first hollow female portion of the female single channel fluid connector of the first type,
wherein the first structure of the second type male single channel fluid connector is constructed and arranged to at least partially cross-sectionally overlap the second structure of the second type female single channel fluid connector when the second type male single channel fluid connector and the second type female single channel fluid connector are aligned along a common center line such that any engagement is prevented between the second type male single channel fluid connector and the second type female single channel fluid connector.

12. The fluid connection system according to claim 11, wherein the first structure extends around the whole circumference of the hollow male portion.

13. The fluid connection system according to claim 11, wherein the second structure has a shape of a sleeve.

14. The fluid connection system according to claim 11, wherein the second hollow male portion of the second type single channel fluid male connector is an inner hollow male portion, and the male connector body is defining an outer collar surrounding the second hollow male portion and spaced radially therefrom, the outer collar is internally threaded, wherein the first structure is extending radially from the exterior of the outer collar, and wherein the female hollow portion of the second type single channel fluid female connector has an external thread.

15. The fluid connection system according to claim 14, wherein the first structure and the second structure are constructed and arranged such that the first structure and the second structure radially and circumferentially at least partly overlap when a center line of the second type male single channel fluid connector and the second type female single channel fluid connector, respectively, are aligned and a thread opening of the internal thread of the second type male single channel fluid connector is aligned with a thread start of the external thread of the second type female single channel fluid connector.

16. The fluid connection system according to claim 14, wherein an inner radius of the second structure is greater than an outer radius of the outer collar but smaller than an outer radius of the first structure, and an outer radius of the second structure is greater than the outer radius of the outer collar.

17. A system comprising:
the fluid connection system according to claim 11;
an arterial line and a venous line connected to a blood treatment unit;
a dialysis fluid line connected to the blood treatment unit for infusion of dialysis fluid from a dialysis fluid bag;
an effluent fluid line connected to the blood treatment unit for passing effluent fluid to an effluent fluid bag;
an infusion fluid line connected to the arterial line for infusion of fluid from an infusion fluid bag or anticoagulant fluid bag; and
a post replacement fluid line connected to the venous line for infusion of replacement fluid from a replacement fluid bag, wherein the dialysis fluid line is arranged with a female single channel fluid connector of the second type, the dialysis fluid bag is arranged with a male single channel fluid connector of the first type, the effluent fluid line is arranged with a female single channel connector of the second type, the effluent fluid bag is arranged with a male single channel fluid connector of the first type, the infusion fluid line is arranged with a female single channel fluid connector of the first type, the infusion fluid bag or anticoagulant bag is arranged with a male single channel fluid connector of the second type, the post replacement fluid line is arranged with a female single channel fluid connector of the second type and the replacement fluid bag is arranged with a male single channel fluid connector of the first type.

* * * * *